US011195262B2

(12) United States Patent
Lin et al.

(10) Patent No.: US 11,195,262 B2
(45) Date of Patent: Dec. 7, 2021

(54) BODY REGION IDENTIFICATION DEVICE AND METHOD

(71) Applicant: COHESION INFORMATION TECHNOLOGY CORP., New Taipei (TW)

(72) Inventors: Feng-Mao Lin, New Taipei (TW);
Chi-Wen Chen, New Taipei (TW);
Wei-Da Huang, New Taipei (TW);
Liangtsan Gary Wu, New Taipei (TW)

(73) Assignee: COHESION INFORMATION TECHNOLOGY CORP., New Taipei (TW)

( * ) Notice: Subject to any disclaimer, the term of this patent is extended or adjusted under 35 U.S.C. 154(b) by 0 days.

(21) Appl. No.: 16/884,408

(22) Filed: May 27, 2020

(65) Prior Publication Data
US 2020/0380659 A1    Dec. 3, 2020

(30) Foreign Application Priority Data

Jun. 3, 2019    (TW) .................................. 108119246

(51) Int. Cl.
*G06K 9/00* (2006.01)
*G06T 7/00* (2017.01)
(Continued)

(52) U.S. Cl.
CPC ........ *G06T 7/0002* (2013.01); *G06K 9/00362* (2013.01); *G06K 9/46* (2013.01);
(Continued)

(58) Field of Classification Search
CPC ........... G06K 2209/05; G06K 9/00208; G06K 9/00362; G06K 9/3216; G06K 9/46; G06K 9/6273; G06N 3/0454; G06N 3/08; G06T 2207/10081; G06T 2207/20076; G06T 2207/20081; G06T 2207/20084; G06T 2207/30012; G06T 2207/30061; G06T 7/0002; G06T 7/0012; G16H 30/20; G16H 30/40; G16H 50/20; G16H 50/70

See application file for complete search history.

(56) References Cited

U.S. PATENT DOCUMENTS

2016/0267222 A1*  9/2016  Larcom ................... G16H 30/20
2016/0300351 A1*  10/2016  Gazit ....................... G06T 7/187
(Continued)

FOREIGN PATENT DOCUMENTS

CN            107403446 A      11/2017

*Primary Examiner* — Xin Jia
(74) *Attorney, Agent, or Firm* — ScienBiziP, P.C.

(57) ABSTRACT

A method for identifying a body region in a medical image includes obtaining a medical image including a number of consecutive bio-section images, inputting the medical image into a preset machine learning model to obtain a numerical value for each of the bio-section images corresponding to the body region to which the bio-section image belongs, determining whether the numerical values of the medical image are abnormal, adjusting the numerical values when the numerical values are abnormal, determining the body region corresponding to the numerical values or the adjusted numerical values, and labeling the body region in the medical image and outputting the labeled medical image. The bio-section images are cross-sectional images of a living body.

16 Claims, 16 Drawing Sheets

(51) Int. Cl.
*G16H 30/20* (2018.01)
*G16H 30/40* (2018.01)
*G16H 50/20* (2018.01)
*G06K 9/46* (2006.01)
*G06N 3/08* (2006.01)

(52) U.S. Cl.
CPC ............... *G06N 3/08* (2013.01); *G16H 30/20* (2018.01); *G16H 30/40* (2018.01); *G16H 50/20* (2018.01); *G06K 2209/05* (2013.01); *G06T 2207/10081* (2013.01); *G06T 2207/20081* (2013.01)

(56) References Cited

U.S. PATENT DOCUMENTS

| | | | |
|---|---|---|---|
| 2016/0328855 A1* | 11/2016 | Lay | G06K 9/4614 |
| 2018/0144828 A1 | 5/2018 | Baker | |
| 2020/0258243 A1* | 8/2020 | Chang | A61B 5/7267 |
| 2020/0411164 A1* | 12/2020 | Donner | G16H 30/20 |

* cited by examiner

BODY REGION IDENTIFICATION DEVICE AND METHOD

FIELD

The subject matter herein generally relates to a device and method for identifying a scanned body region.

BACKGROUND

Computed Tomography (CT) and other medical imaging techniques have become important diagnostic methods in modern medicine. Medical images of organisms (such as humans or animal bodies) obtained by CT or other medical imaging techniques are composed of a series of 2D images. Usually, each 2D image is a cross-sectional image of a specific part of the organism, and the series of 2D images are combined to produce a 3D medical image. When scanning the organism, multiple regions of the organism may be scanned, such as from head to neck, from chest to abdomen, or from head to toe. Each region may include hundreds or thousands of cross-sectional images, which are generally manually examined to determine which region of the organism the cross-sectional image belongs. Such manual examinations require a large amount of human resources. On the other hand, although machine learning models have been used to intelligently identify the regions to which the cross-sectional images belong, different factors such as height, size, and shooting position of organisms may cause erroneous identification, which affects diagnosis by medical workers.

BRIEF DESCRIPTION OF THE DRAWINGS

Implementations of the present disclosure will now be described, by way of embodiments, with reference to the attached figures.

DETAILED DESCRIPTION

Figure 1:
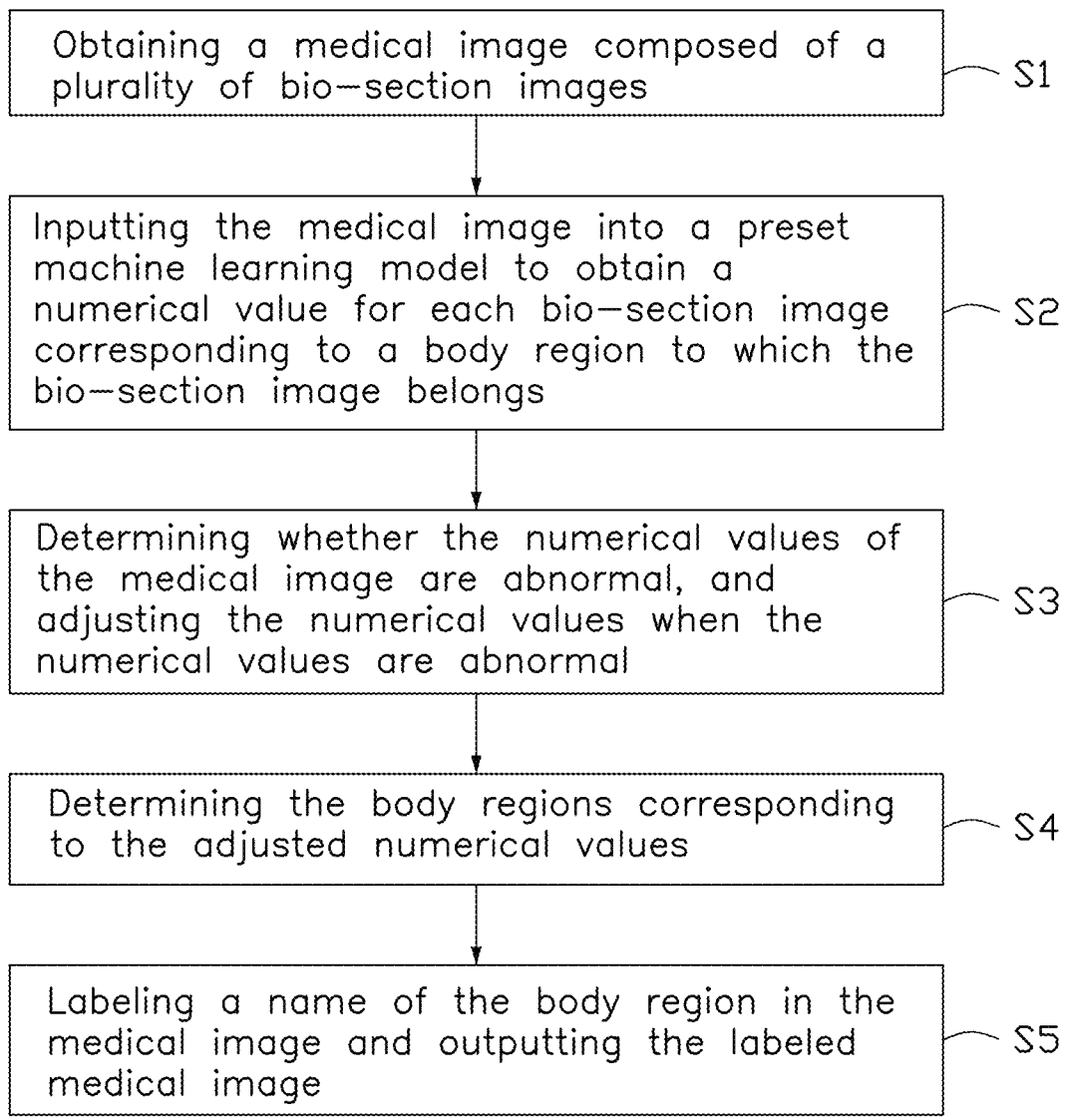
FIG. 1 is a flowchart of an embodiment of a method for identifying a body region in a medical image.

It will be appreciated that for simplicity and clarity of illustration, where appropriate, reference numerals have been repeated among the different figures to indicate corresponding or analogous elements. Additionally, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "comprising" means "including, but not necessarily limited to"; it specifically indicates open-ended inclusion or membership in a so-described combination, group, series and the like.

FIG. 1 shows a flowchart of an embodiment of a method for identifying a body region in a medical image. The order of blocks in the flowchart may be changed according to different requirements, and some blocks may be omitted. For convenience of description, only parts related to the embodiment are described.

At block S1, a medical image is obtained.

Figure 2:
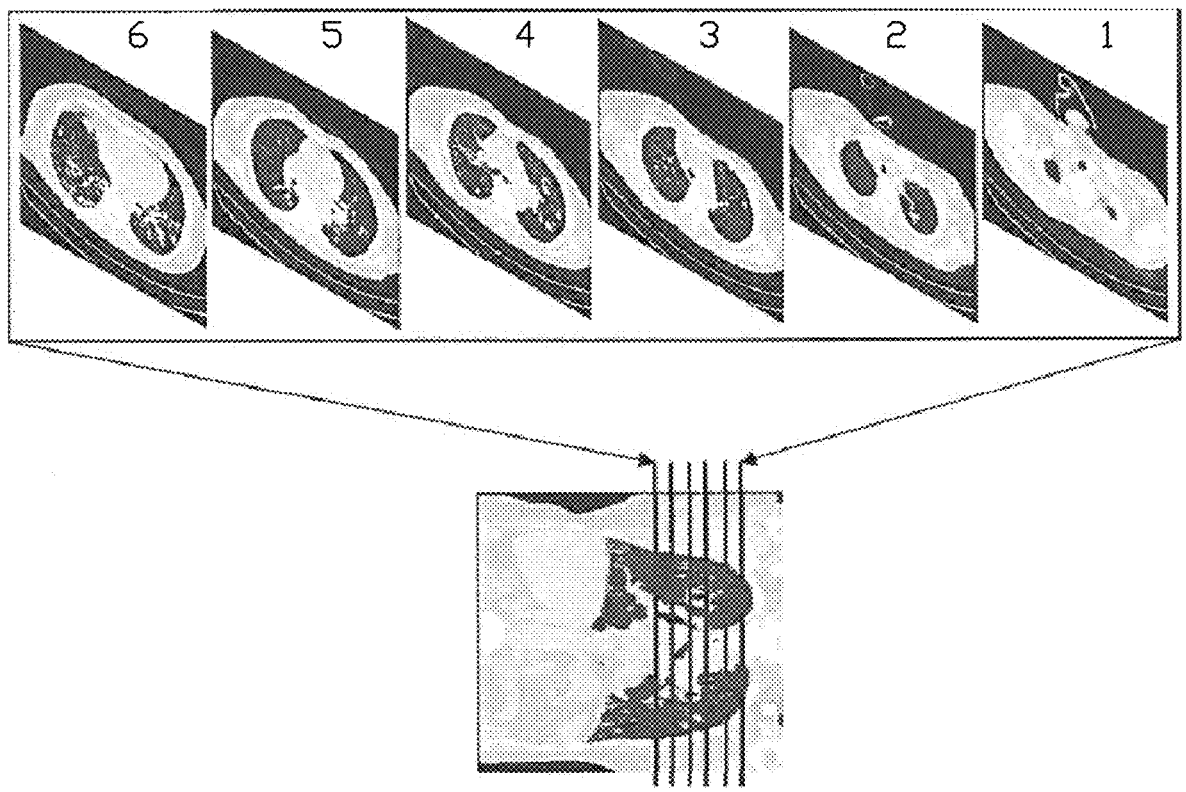
FIG. 2 is a diagram of a medical image composed of a plurality of bio-section images.

The obtained medical image includes a plurality of consecutive cross-sectional images of a living body (hereinafter "bio-section images"). The plurality of continuous bio-section images can be combined to visualize various regions of the living body including the lungs, liver, limbs, and the like. For example, as shown in FIG. 2, a region of the body is visualized by combining first through sixth bio-section images of the body region. Each body region requires a corresponding quantity of bio-section images to be captured. For example, the body region containing the lungs requires an N number of bio-section images, and the body region containing the liver requires an M number of bio-section images. For each body region, a first bio-section image corresponds to a top-most layer of the body region, and a last bio-section image corresponds to a bottom-most layer of the body region.

Each of the bio-section images may be image data conforming to the Digital Imaging and Communications in Medicine (DICOM) standard. DICOM is a standard that regulates how to process, store, print, and transmit medical image data. DICOM's standards include file format definitions and communication protocols. Image data conforming to the DICOM standard must be transmitted over a communication network that supports the TCP/IP protocol. Image data conforming to the DICOM standard has a format definition such as pixel data and image attribute information. Pixel data describes the value of each pixel to form an image. The attribute information has a plurality of tags and a plurality of attribute values respectively corresponding to the tags.

In one embodiment, the obtained medical image is a computed tomography image (CT image).

The medical image may include bio-section images of the entire human body, or may include a series of continuous bio-section images of a specific body region, such as from the head to the neck, or the chest and abdomen of a patient.

At block S2, the medical image is input into a preset machine learning model to obtain a numerical value for each of the bio-section images corresponding to the body region to which the bio-section image belongs.

In one embodiment, the preset machine learning model may be a neural network model, such as a Residual Networks (ResNets) learning model, or a convolutional neural network model (AlexNet, VGG16, or VGG19). The medical image and a sequence of the bio-section images are input into the preset machine learning model. By training the preset machine learning model, a numerical value corresponding to each of the bio-section images is output, and the body region to which each of the bio-section images belongs is determined according to the numerical value. The training method of the machine learning model can be implemented using the related art, for example, KeYan et al. in UNSUPERVISED BODY REGION REGESSION VIA SPATIALLY SELF-ORDERING CONVOLUTIONAL NEURAL NETWORKS, (2018), arXiv: 1707.03891 v2 [cs. CV].

Figure 3:
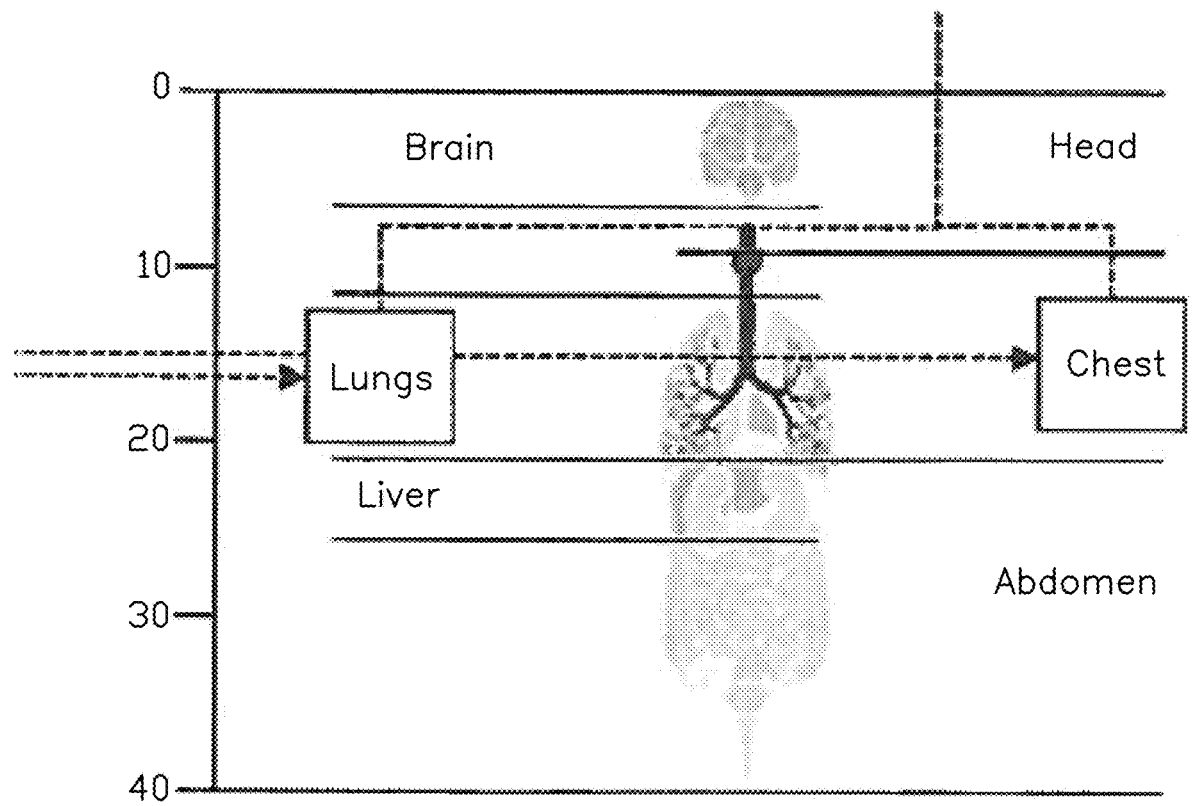
FIG. 3 is a diagram of a range of numerical values corresponding to different body regions.

FIG. 3 shows a diagram of a numerical range of 0-40 corresponding to different body regions of the human body. For example, a range of 1-10 corresponds to the head of the human body, a range of 10-20 corresponds to the chest of the human body, and a range of 20-40 corresponds to the abdomen of the human body. Within the chest, a range of 17-20 contains the lungs. When a bio-section image is input into the machine learning model and the numerical value corresponding to the bio-section image is 17, the corresponding body region contains the lungs.

At block S3, whether the numerical values of the medical image are abnormal is determined, and the numerical values are adjusted when the numerical values are abnormal.

When the body region corresponding to the bio-section image is identified by the machine learning model, an error may occur. For example, the numerical value corresponding to the body region containing the lungs may be incorrectly assigned to the body region containing the liver. If the abnormal numerical values are not detected and adjusted, the machine learning model will have inaccurate recognition results for the body regions. Therefore, it is necessary to perform overall anomaly detection and adjustment processing on the numerical values output by the machine learning model, as described with reference to FIGS. 7-8.

At block S4, the body region corresponding to the adjusted numerical value is determined.

At block S5, the name of the body region in the medical image is labeled, and the labeled medical image is output.

In one embodiment, the name of the body region is labeled directly in the medical image. For example, if it is determined that the medical image contains the liver, the label of the liver is added to the medical image. The label may include Chinese characters, English letters, and the like.

In one embodiment, before the medical image is input into the preset machine learning model at block S2, the medical image may be pre-processed, so that the pre-processed medical image is more favorable for recognition and classification of the machine learning model, thereby reducing a training time of the model and improving training efficiency.

Figure 4:
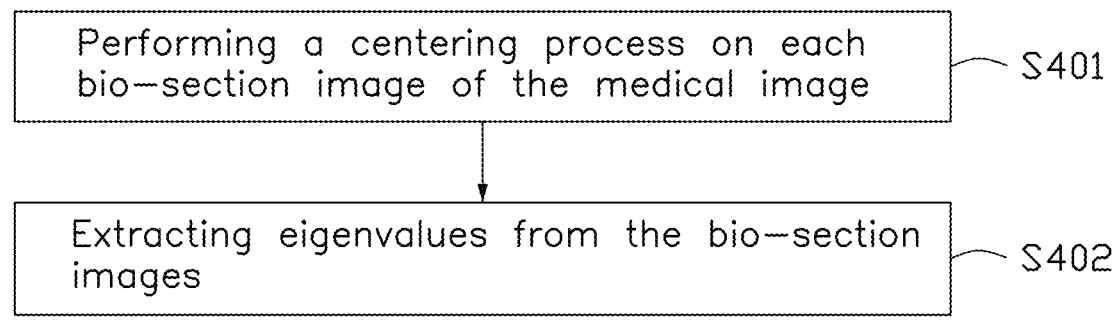
FIG. 4 is a flowchart of an embodiment of a method for pre-processing the medical image.

FIG. 4 shows a flowchart of an embodiment of a method for pre-processing the medical image. The method of pre-processing the medical image may include the following blocks.

At block S401, a centering process is performed on each of the bio-section images of the medical image.

In the process of capturing the medical image, due to a patient's position and body shape, the body region may not be in a proper position in the medical image. For example, the patient's spine may have scoliosis, or some of the body regions may be offset in the medical image, which is not conducive to recognition and training by the machine learning model. Thus, when the body region in the bio-section image is centered, the problem of the body region being offset in the image can be corrected, which is beneficial to the machine learning model to recognize and interpret the image. The method of the centering process is described with reference to FIG. 5.

At block S402, eigenvalues are extracted from the bio-section images.

A bio-section image may include various components such as bones, body fluids, soft tissues, muscles, and air. CT values of pixels belonging to different components are different, and pixel values of the different components are different. In general, when the bio-section image is more complex, the machine learning model requires a longer time to train. In addition, a general model can be trained by blurring a small number of image states. By extracting eigenvalues of each of the bio-section images, the bio-section image is simplified to make the vital organs or tissues stand out, thereby reducing training time and improving efficiency. A method of extracting eigenvalues is described with reference to FIG. 6.

Figure 5:
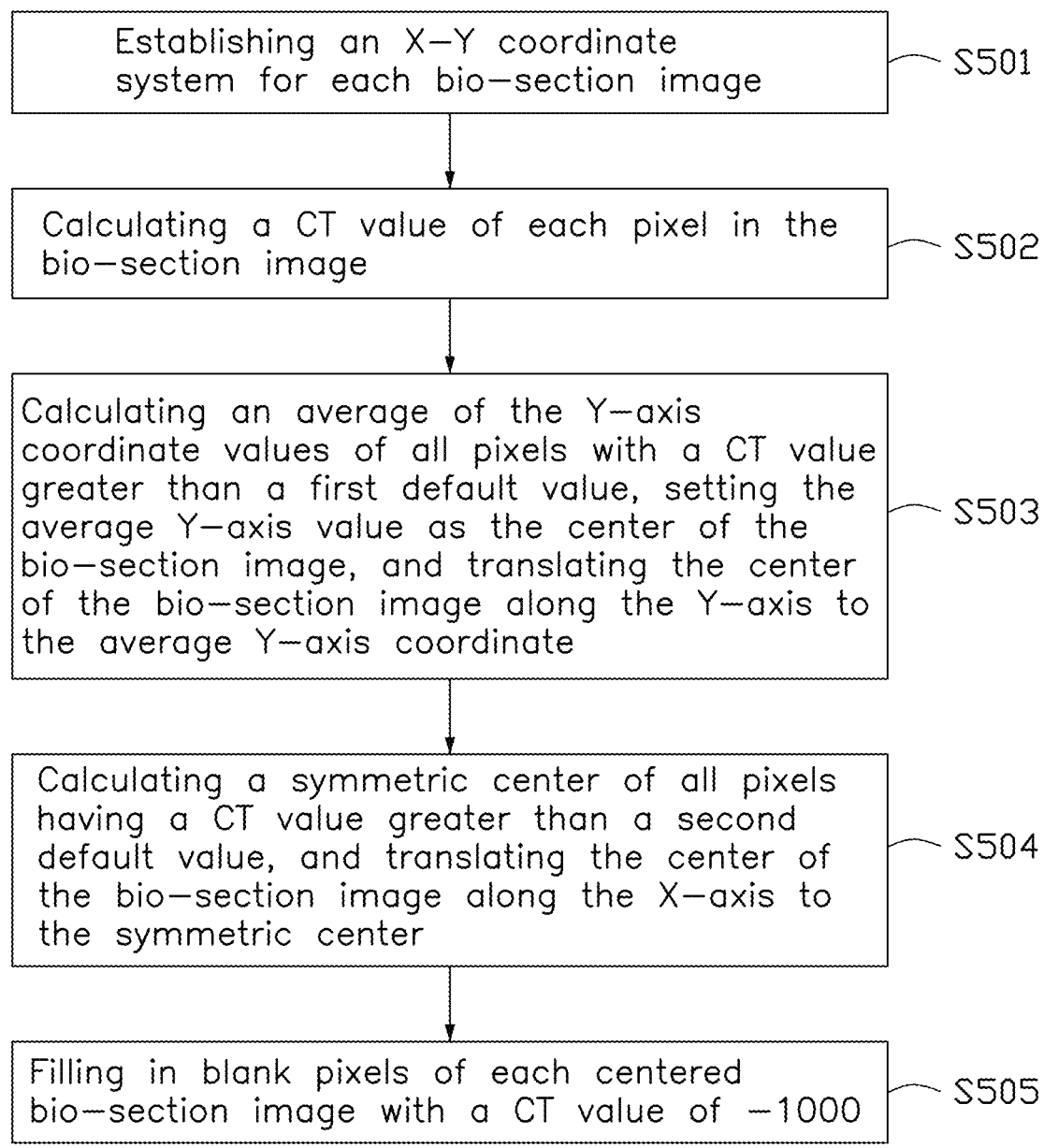
FIG. 5 is a flowchart of a method of performing a centering process on the bio-section images.

FIG. 5 shows a flowchart of a method of performing a centering process on the bio-section images as described in block S401.

At block S501, an X-Y coordinate system is established for each of the bio-section images, wherein all of the bio-section images correspond to one coordinate region.

In one embodiment, the X coordinate axis of the coordinate system may be the bottom edge of the bio-section image, and the Y coordinate axis may be the left edge of the bio-section image.

At block S502, a CT value of each pixel in the bio-section image is calculated.

The CT value is an X-ray attenuation coefficient corresponding to tissue in the bio-section image and is a unit of measurement for measuring density of the tissue. A unit of measurement of the CT value may be the Hournsfield unit (HU). The CT value of air is −1000, and the CT value of dense bone is +1000.

At block S503, an average of the Y-axis coordinate value of all pixels with a CT value greater than a first default value is calculated, the average Y-axis coordinate value is set as the center of the bio-section image, and the center of the bio-section image is translated along the Y-axis to the average Y-axis coordinate.

In one embodiment, the first default value is −90, so that the average of the Y-axis coordinate values of all pixels greater than −90 HU is calculated. In other embodiments, the first default value may be set as needed.

At block S504, a symmetric center of all pixels having a CT value greater than a second default value is calculated, and the center of the bio-section image is translated along the X-axis to the symmetric center.

In one embodiment, the second default value is 200.

At block S505, blank pixels of each centered bio-section image are filled in with a CT value of −1000.

After the bio-section image is centered, a portion of the bio-section image is translated out of the original coordinate region. Correspondingly, a blank portion is generated in the original coordinate region. The blank region is filled with pixels having a CT value of −1000 so that the machine learning model can recognize the centered bio-section image.

Figure 6:
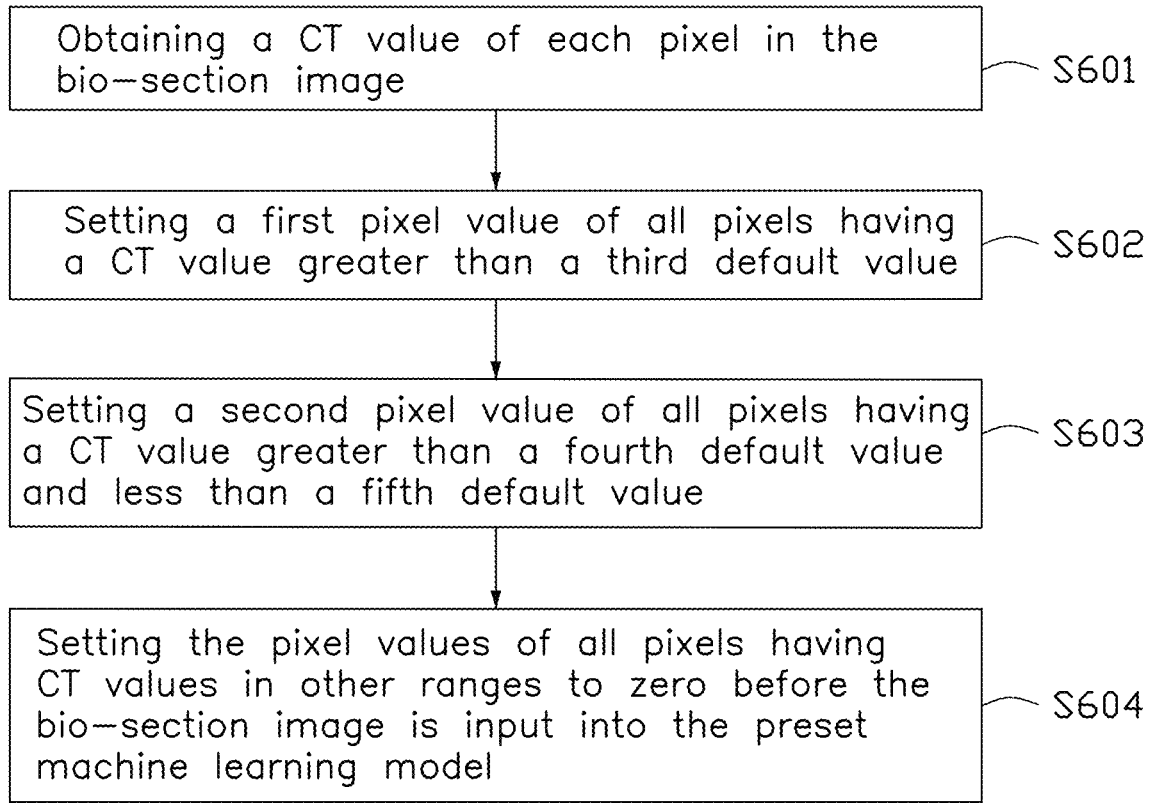
FIG. 6 is a flowchart of a method of extracting eigenvalues of the bio-section images.

FIG. 6 shows a flowchart of a method of extracting eigenvalues of the bio-section images at block S402.

At block S601, a CT value of each pixel in each of the bio-section images is obtained.

At block S602, pixels having a CT value greater than a third default value are set to a first pixel value.

In one embodiment, the third default value is 200 HU, and the pixels having a CT value greater than 200 HU correspond to bone of the patient. In other embodiments, the third default value may be set as another value for indicating bone as needed.

At block S603, pixels having a CT value between a fourth default value and a fifth default value are set to a second pixel value. The fifth default value is less than the third default value and greater than the fourth default value. The second pixel value is less than the first pixel value.

The pixels having a CT value between the fourth default value and the fifth default value correspond to body fluid, soft tissue, muscle, or the like of the patient. In one embodiment, the fourth default value is −5 HU and the fifth default value is 50 HU. In another embodiment, the fourth default value and the fifth default value may be set as other CT values as needed.

In one embodiment, the first pixel value is 1, and the second pixel value is 0.5.

At block S604, before the bio-section image is input into the preset machine learning model, the pixel values of all pixels having CT values in other ranges are set to zero.

In another embodiment, the bio-section images are pre-processed by the centering process, and the method of extracting the eigenvalues is omitted.

In another embodiment, the bio-section images are pre-processed by extracting the eigenvalues, and the method of centering the bio-section images is omitted.

Figure 7:
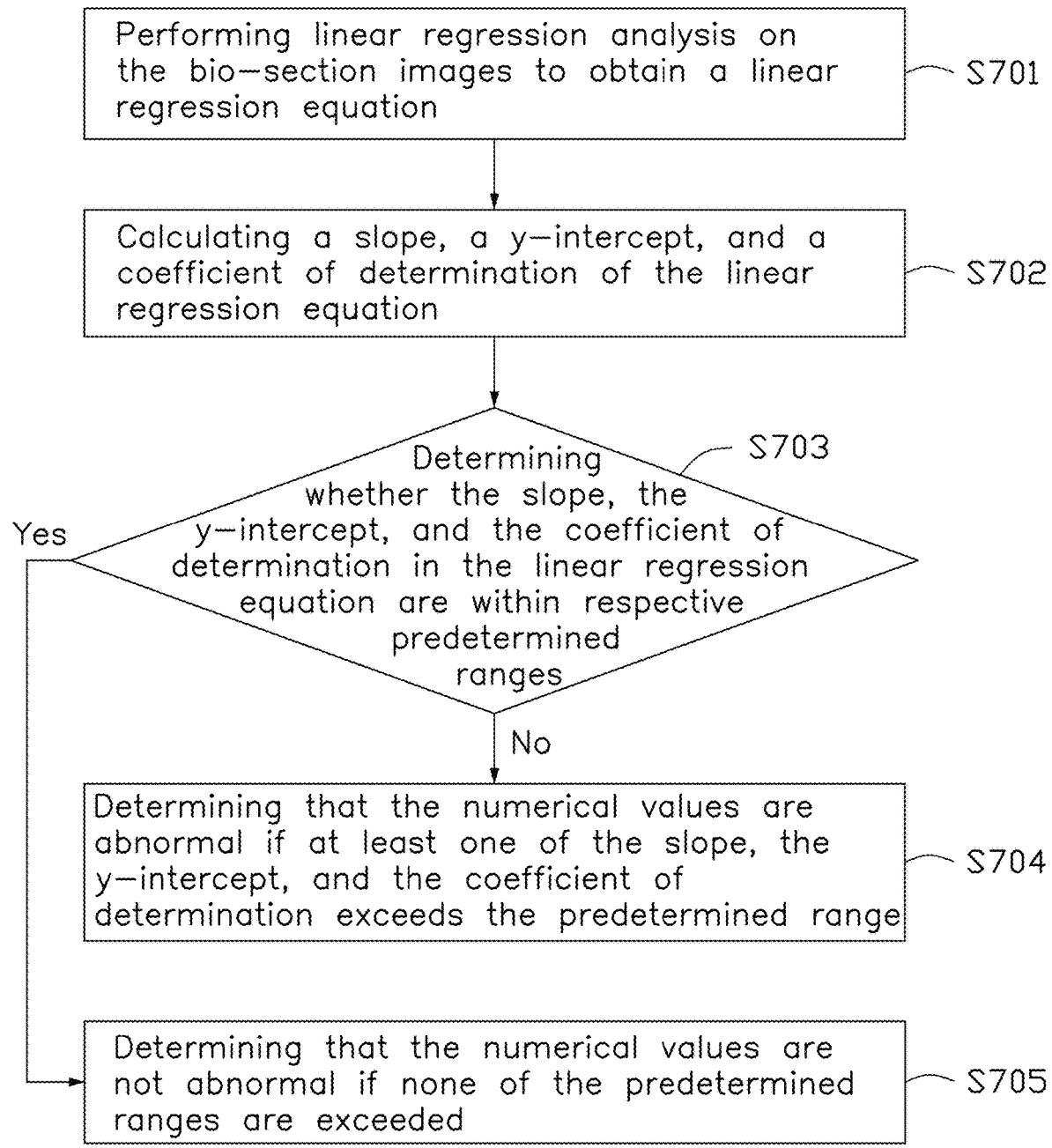
FIG. 7 is a flowchart of a method for detecting whether the numerical values of the medical image are abnormal.

FIG. 7 shows a flowchart of a method for detecting whether the numerical values of the medical image are abnormal at block S3 in FIG. 1.

At block S701, linear regression analysis is performed on the bio-section images to obtain a linear regression equation. CT scan numbers are set as the independent variable, and the numerical values corresponding to the body region assigned to the bio-section images are set as the dependent variable.

In one embodiment, a sequence of the CT scan numbers is sequentially ordered according to DICOM SliceLocation values in the medical image from largest to smallest or from smallest to largest according to an imaging direction or the patient's position. For example, the CT scan numbers may be sequentially arranged from 0 to 1, 2, 3, 4, . . . n.

At block S702, a slope, a y-intercept, and a coefficient of determination of the linear regression equation are calculated.

At block S703, whether the slope, the y-intercept, and the coefficient of determination in the linear regression equation are within respective predetermined ranges is determined.

The predetermined ranges of the slope, the y-intercept, and the coefficient of determination may be set according to actual needs. In one embodiment, the predetermined range of the coefficient of determination is greater than 0.8. Generally, a slope approaching 0 means a greater number of bio-section images are assigned the same body region.

At block S704, if at least one of the slope, the y-intercept, and the coefficient of determination exceeds the respective predetermined range, it is determined that the numerical values are abnormal.

At block S705, if none of the predetermined ranges are exceeded, it is determined that the numerical values are not abnormal.

Figure 8:
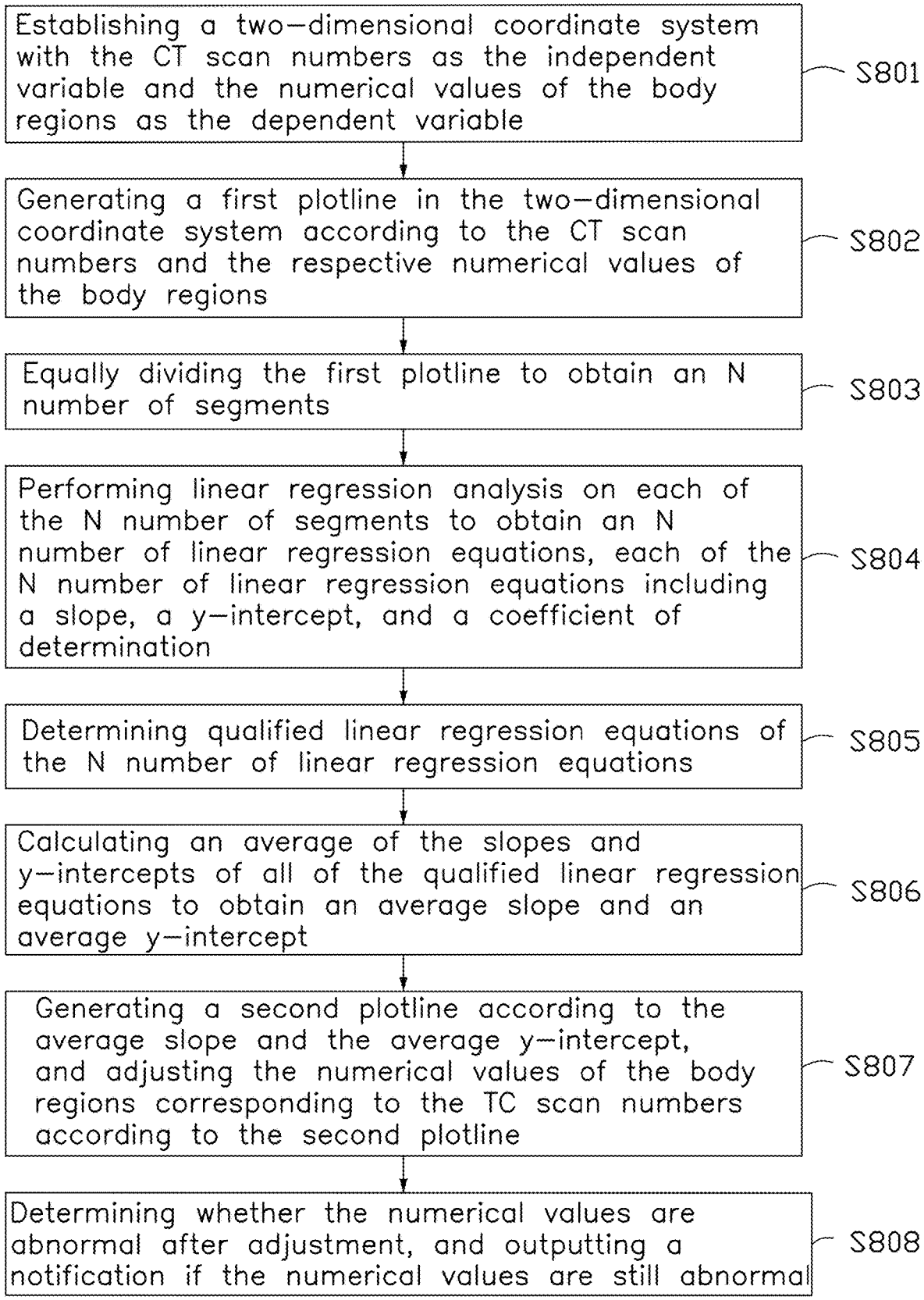
FIG. 8 is a flowchart of a method for adjusting the numerical values of the medical image.

FIG. 8 shows a flowchart of a method for adjusting the numerical values of the medical image.

At block S801, a two-dimensional coordinate system is established with the CT scan number as the independent variable and the numerical value of the body region as the dependent variable.

At block S802, a first plotline is generated in the two-dimensional coordinate system according to the CT scan numbers and the respective numerical values of the body regions.

At block S803, the first plotline is equally divided to obtain an N number of segments.

N is a positive integer greater than two. In one embodiment, the first plotline may be divided into four segments. In other embodiments, the first plotline may be equally divided into more or less segments as needed.

At block S804, linear regression analysis is performed on each of the N number of segments to obtain an N number of linear regression equations, respectively. Each of the N number of linear regression equations includes a slope, a y-intercept, and a coefficient of determination.

At block S805, qualified linear regression equations of the N number of linear regression equations are determined. The qualified linear regression equations are the linear regression equations of the N number of linear regression equations in which the slope, the y-intercept, and the coefficient of determination are respectively within the predetermined ranges.

At block S806, an average of the slopes and y-intercepts of all of the qualified linear regression equations is calculated to obtain an average slope and an average y-intercept.

At block S807, a second plotline is generated according to the average slope and the average y-intercept. The numerical value of the body region corresponding to the CT scan number may be adjusted according to the second plotline.

At block S808, whether the numerical values are abnormal after adjustment is determined. If the numerical values are abnormal, a notification is output to notify relevant personnel to perform manual adjustment.

For example, FIGS. 9A-9F show diagrams of abnormality detection and adjustment.

Figure 9A:
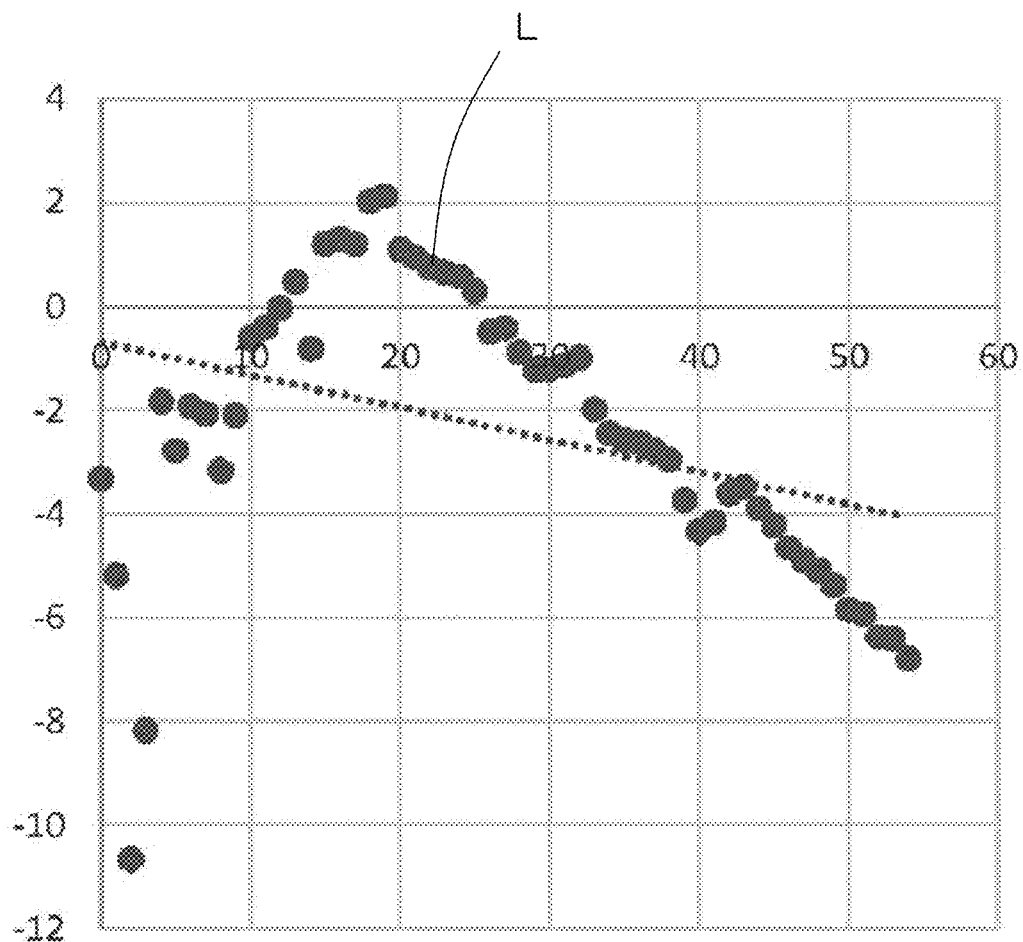
FIG. 9A is a first plotline composed of discrete points corresponding to a relationship between TC scan numbers and the corresponding numerical values of the body regions.
Figure 9B:
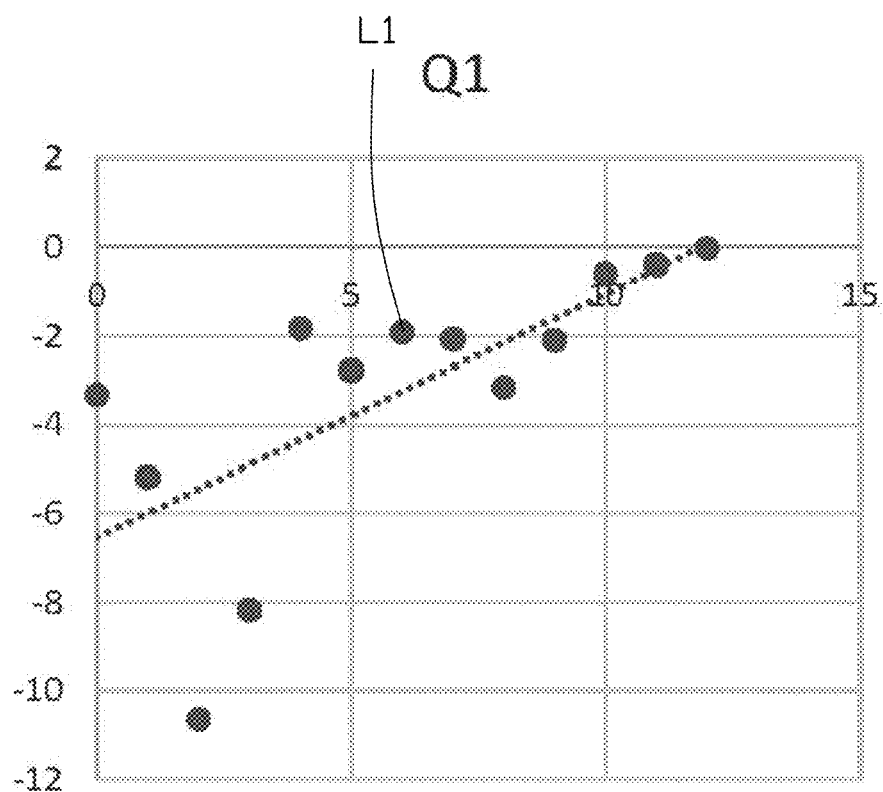
FIGS. 9B, 9C, 9D, and 9E are plotlines of divided segments of the first plotline in FIG. 9A.
Figure 9C:
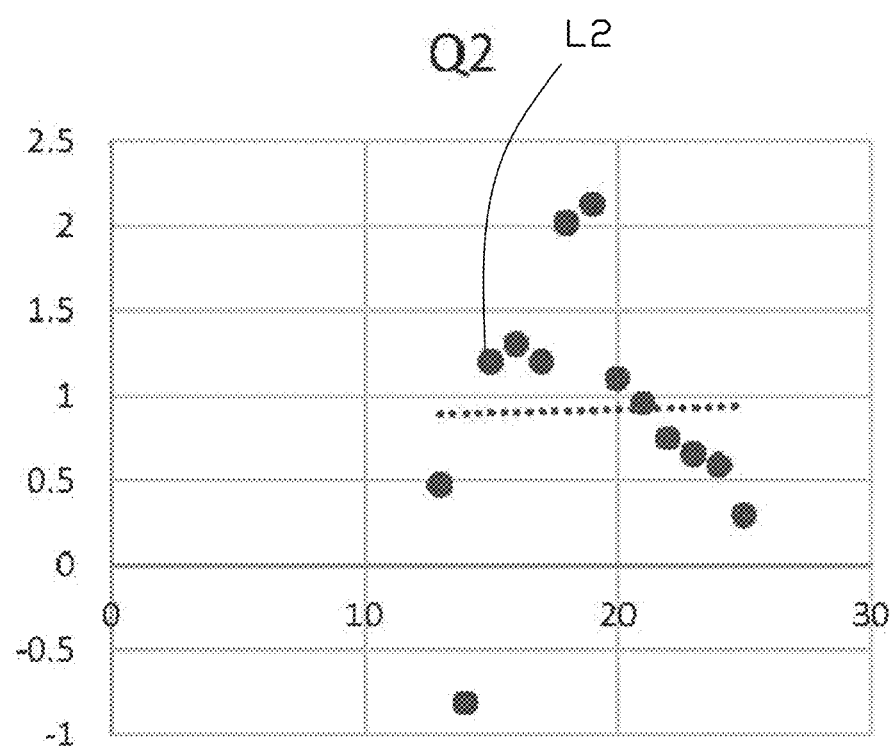
Figure 9D:
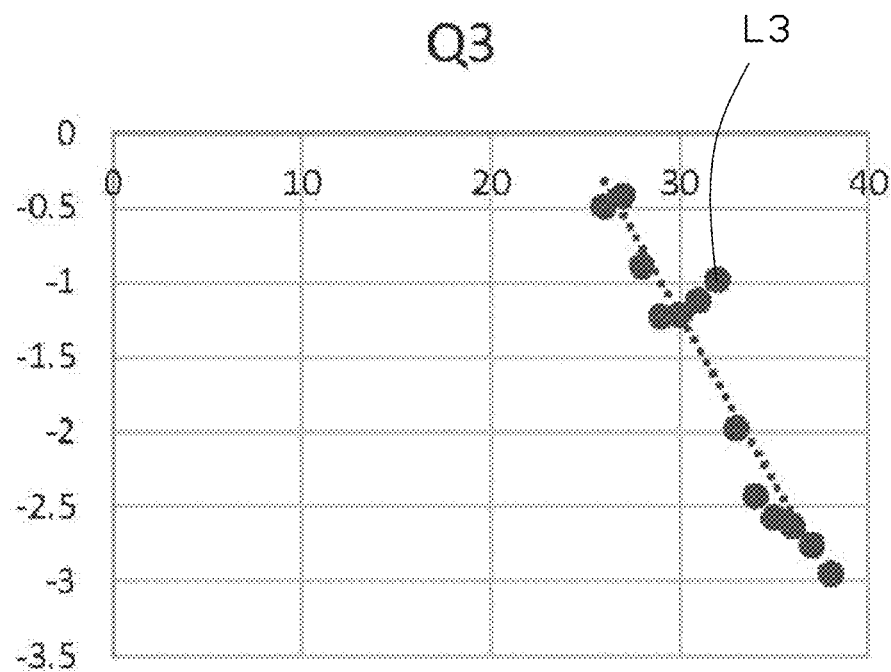
Figure 9E:
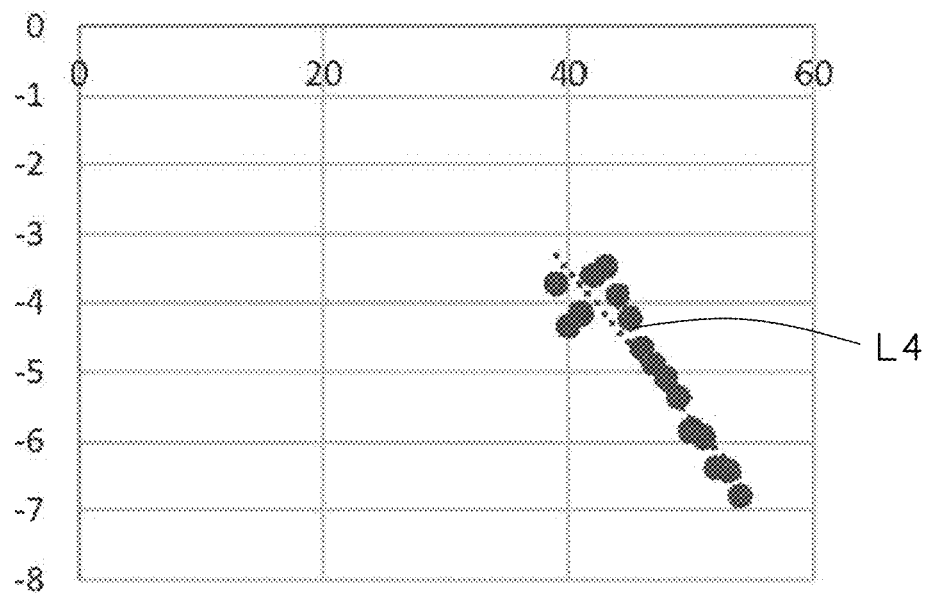

In FIG. 9A, L is a plotline composed of discrete points corresponding to the relationship between the CT scan number and the corresponding numerical value of the body region before correction (the first plotline). The linear regression equation generated according to the first plotline is: y=0.1412x-23.426, and the calculated coefficient of determination is 0.6796. Thus, the numerical values are abnormal.

Figure 9F:
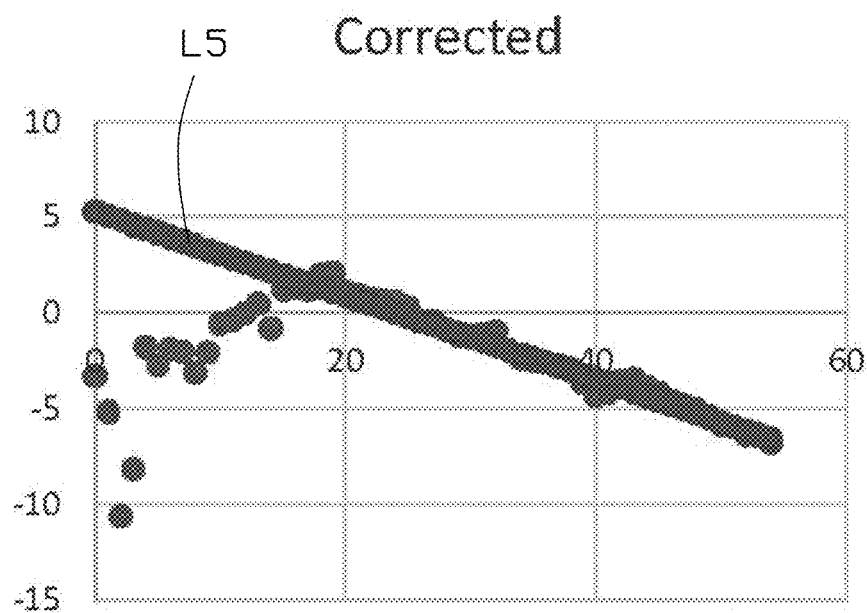
FIG. 9F is a second plotline calculated according to the plotlines in FIGS. 9B-9E.

As shown in FIGS. 9B-9E, the first plotline is equally divided into four segments L1-L4. The linear regression equations of the four segments are respectively calculated to obtain the slope, the y-intercept, and the coefficient of determination of each segment. The linear regression equation of the first segment L1 is y=0.0369x-20.486 with a coefficient of determination of 0.7559. The linear regression equation of the second segment L2 is y=0.099x-22.183 with a coefficient of determination of 0.9608. The linear regression equation of the third segment L3 is y=0.0988x-22.683 with a coefficient of determination of 0.942. The linear regression equation of the fourth segment is y=0.0885x-15.288 with a coefficient of determination of 0.0196. The slope, the y-intercept, and the coefficient of determination of the third segment L3 and the fourth segment L4 are within the respective predetermined ranges, so the average value of the slopes and the average value of the y-intercepts of the third segment L3 and the fourth segment L4 are calculated to obtain the plotline L5 as shown in FIG. 9F. The plotline L5 represents the second plotline, which is used to adjust the numerical values of the body regions assigned to the respective CT scan numbers.

Figure 10:
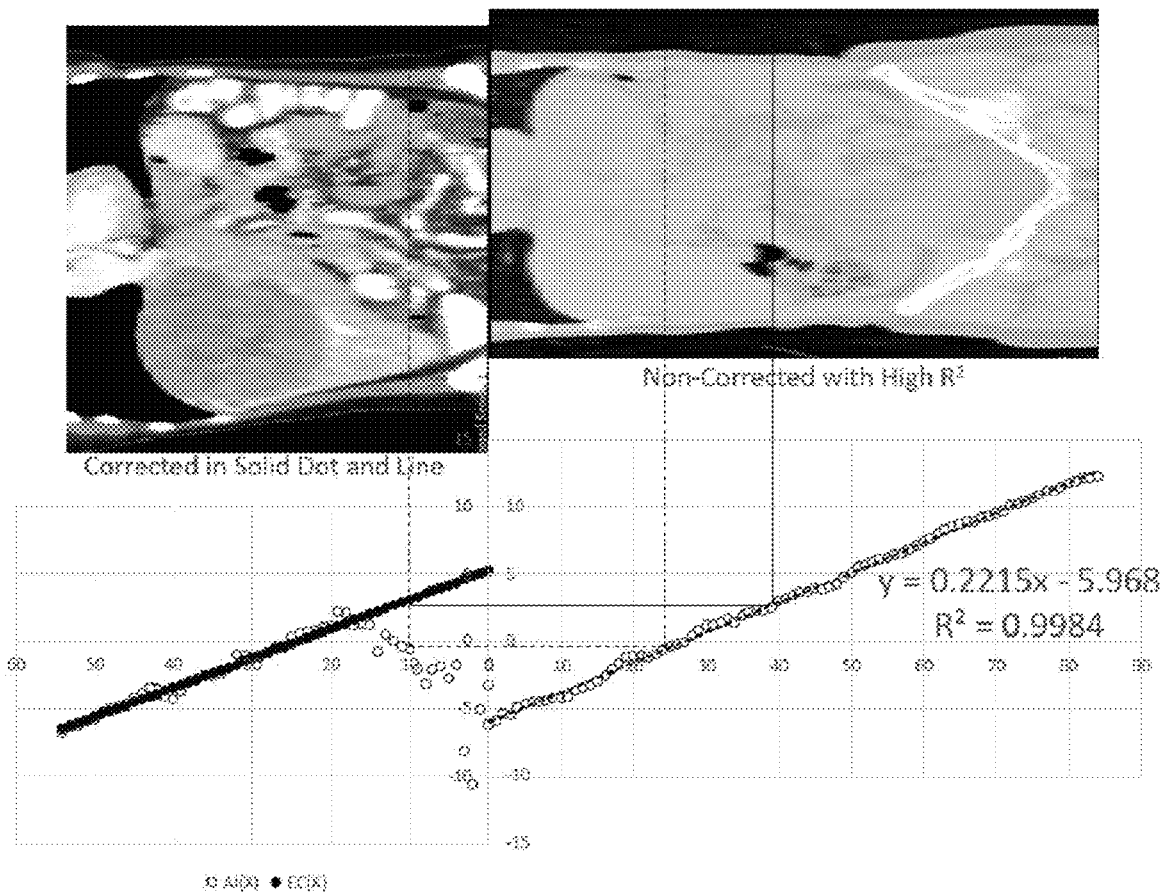
FIG. 10 is a view showing a medical image obtained by adjusting the numerical values of a body part according to FIGS. 9A-9F.

As shown in FIG. 10, the plot points AI(X) are the numerical values before adjustment. A left position of the liver on the left corresponds to a middle position of the liver on the right. The plotline EC(X) is the adjusted numerical values. The left and right images correspond to a lower part of the liver, indicating that this algorithm can correctly adjust the numerical values.

Figure 11:
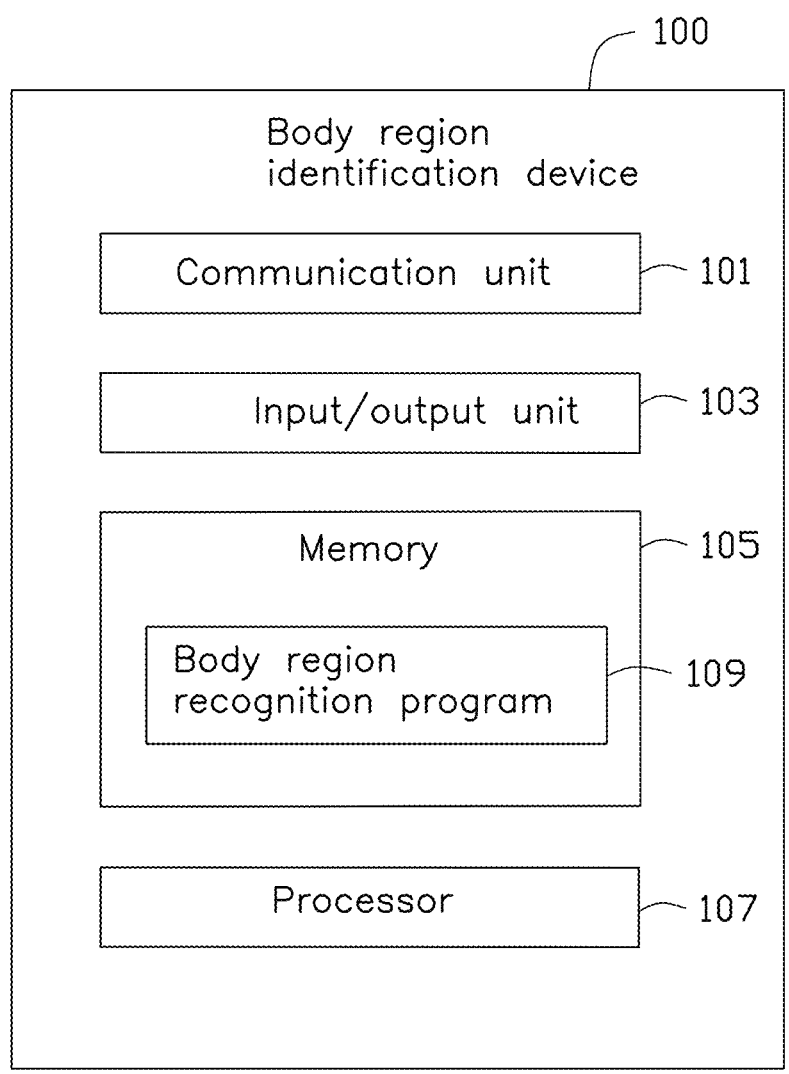
FIG. 11 is a block diagram of a body region identification device.

FIG. 11 shows a schematic diagram of a body region identification device 100.

The body region identification device 100 (hereinafter referred to as "the identification device 100") includes a communication unit 101, an input/output unit 103, a memory 105, and a processor 107. The identification device 100 may be, but is not limited to, any one of a server, a desktop computer, a notebook computer, an all-in-one computer, a tablet computer, a smart phone, or a medical image capturing device. The server may be, but is not limited to, a single server, a server cluster, or a cloud server.

The communication unit 101 may be an electronic module including necessary hardware, software, or firmware, and is configured to establish data exchange with other communication devices through a communication network. For example, in some embodiments, the communication unit 101 can establish a communication connection with a medical image capturing device, and receive the medical image including the bio-section images of the body region from the medical image capturing device. In other embodiments, the communication unit 101 may also establish a connection with the server, acquire the medical image from the server, and upload the recognition result to the server. In still other embodiments, the communication unit 101 can also perform data interaction with a user terminal (e.g., a smart phone, a personal calculator, etc.), such as sending a recognition result to the user terminal. The communication network can include at least one of a wired network and a wireless network. The wireless network and the wired network may be any network existing in the related art and appearing in the future for the identification device 100 to communicate with the medical image capture device or server. In other embodiments, the communication unit 101 may also be omitted when the identification device 100 is in the medical image capturing device itself.

The input/output unit 103 is configured to receive a control instruction input by a user and output a data processing result. In this embodiment, the input/output unit 103 may include an independent input device (such as a mouse, a keyboard, a tablet, a voice recognition device, etc.) and an output device (such as a liquid crystal display, a printer, etc.), and may also be a touch display screen. For example, the input/output unit 103 can receive an instruction for acquiring and recognizing a medical image input by a user through one of a mouse, a keyboard, or a voice recognition device, and pass the medical image result whose identification is completed and marked with a body region name through the display device. The medical image is output to the user or printed out by the printer and output to the user.

The memory 105 stores a body region recognition program 109 and various data such as medical image data. The memory 105 can be, but is not limited to, a read-only memory (ROM), a random access memory (RAM), a programmable read-only memory (PROM), an erasable programmable read-only memory (EPROM), etc.

The processor 107 can be an electronic module, such as a server, that includes one or more hardware, software, or firmware. These servers can be deployed in a centralized or distributed cluster. In other implementations, the processor 107 may be a central processing unit (CPU) in a single computer, or may be a digital signal processor (DSP), an application specific integrated circuit (ASIC), Field-Programmable Gate Array (FPGA), etc.

When the processor 107 runs or executes the body region recognition program 109, the methods in FIGS. 1 and 4-8 may be implemented.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. A method for identifying a body region in a medical image, the method comprising:
   obtaining a medical image comprising a plurality of consecutive bio-section images, the bio-section images being cross-sectional images of a body;
   inputting the medical image into a preset machine learning model and obtaining a numerical value for each of the bio-section images corresponding to a region of the body to which the bio-section image belongs;
   determining whether the numerical values of the medical image are abnormal, and adjusting the numerical values when the numerical values are abnormal;
   determining the body region corresponding to the numerical values or the adjusted numerical values; and
   labeling the body region in the medical image and outputting the labeled medical image.

2. The method of claim 1, further comprising:
   pre-processing the medical image by at least one of a centering process and an eigenvalue extraction process before inputting the medical image into the machine learning model.

3. The method of claim 2, wherein the method of pre-processing the medical image by the centering process comprises:
   establishing an X-Y coordinate system for each of the bio-section images, wherein all of the bio-section images correspond to one coordinate region;
   calculating a Computed Tomography (CT) value of each pixel in each of the bio-section images;
   calculating an average of Y-axis coordinate values of all pixels having a CT value greater than a first default value, setting the average Y-axis coordinate value as a center of the bio-section image, and translating the center of the bio-section image along the Y-axis to the average Y-axis coordinate;
   calculating a symmetric center of all pixels having a CT value greater than a second default value, and translating the center of the bio-section image along the X-axis to the symmetric center; and
   filling in blank pixels of each centered bio-section image by setting a CT value of the blank pixels to −1000.

4. The method of claim 2, wherein the method of pre-processing the medical image by the eigenvalue extraction process comprises:
   obtaining a CT value of each pixel in each of the bio-section images;

setting pixels having a CT value greater than a third default value to a first pixel value;

setting pixels having a CT value between a fourth default value and a fifth default value to a second pixel value, wherein the fifth default value is less than the third default value and greater than the fourth default value, and the second pixel value is less than the first pixel value; and setting the pixel values of pixels having CT values in other ranges to zero.

5. The method of claim 1, wherein:
the preset machine learning model comprises at least one of a neural network model or a convolutional neural network model.

6. The method of claim 1, wherein a method of determining whether the numerical values of the medical image are abnormal comprises:

performing linear regression analysis on the bio-section images to obtain a linear regression equation, wherein Computed Tomography (CT) scan numbers are set as the independent variable, and the numerical values corresponding to the CT scan numbers are set as the dependent variable;

calculating a slope, a y-intercept, and a coefficient of determination of the linear regression equation;

determining whether the slope, the y-intercept, and the coefficient of determination in the linear regression equation are within respective predetermined ranges;

determining that the numerical values are abnormal if at least one of the slope, the y-intercept, and the coefficient of determination exceeds the respective predetermined range; and determining that the numerical values are not abnormal if none of the predetermined ranges are exceeded.

7. The method of claim 6, wherein the method of adjusting the numerical values comprises:

establishing a two-dimensional coordinate system with the CT scan number as the independent variable and the numerical value of the body region as the dependent variable;

generating a first plotline in the two-dimensional coordinate system according to the CT scan numbers and the respective numerical values of the body regions;

equally dividing the first plotline to obtain an N number of segments;

performing linear regression analysis on each of the N number of segments to obtain an N number of linear regression equations, respectively, wherein each of the N number of linear regression equations comprises a slope, a y-intercept, and a coefficient of determination;

determining qualified linear regression equations of the N number of linear regression equations, wherein the qualified linear regression equations are the linear regression equations of the N number of linear regression equations in which the slope, the y-intercept, and the coefficient of determination are respectively within the predetermined ranges;

calculating an average of the slopes and y-intercepts of all of the qualified linear regression equations to obtain an average slope and an average y-intercept;

generating a second plotline according to the average slope and the average y-intercept, and adjusting the numerical values corresponding to the CT scan numbers according to the second plotline.

8. The method of claim 7, wherein the method of adjusting the numerical values further comprises:

determining whether the numerical values are abnormal after the adjustment; and outputting a notification to perform manual adjustments if the numerical values are abnormal.

9. A body region identification device comprising:
a processor; and
a memory storing a plurality of instructions, which when executed by the processor, cause the processor to:

obtain a medical image comprising a plurality of consecutive bio-section images, the bio-section images being cross-sectional images of a living body;

input the medical image into a preset machine learning model and obtain a numerical value for each of the bio-section images corresponding to the body region to which the bio-section image belongs;

determine whether the numerical values of the medical image are abnormal, and adjust the numerical values when the numerical values are abnormal;

determine the body region corresponding to the numerical values or the adjusted numerical values; and label the body region in the medical image and output the labeled medical image.

10. The body region identification device of claim 9, wherein the processor is further configured to:

pre-process the medical image by at least one of a centering process and an eigenvalue extraction process before inputting the medical image into the machine learning model.

11. The body region identification device of claim 10, wherein the processor pre-processes the medical image by the centering process by:

establishing an X-Y coordinate system for each of the bio-section images, wherein all of the bio-section images correspond to one coordinate region;

calculating a Computed Tomography (CT) value of each pixel in the bio-section image;

calculating an average of Y-axis coordinate values of all pixels having a CT value greater than a first default value, setting the average Y-axis coordinate value as a center of the bio-section image, and translating the center of the bio-section image along the Y-axis to the average Y-axis coordinate;

calculating a symmetric center of all pixels having a CT value greater than a second default value, and translating the center of the bio-section image along the X-axis to the symmetric center; and filling in blank pixels of each centered bio-section image by setting a CT value of the blank pixels to −1000.

12. The body region identification device of claim 10, wherein the processor pre-processes the medical image by the eigenvalue extraction process by:

obtaining a CT value of each pixel in each of the bio-section images;

setting pixels having a CT value greater than a third default value to a first pixel value;

setting pixels having a CT value between a fourth default value and a fifth default value to a second pixel value, wherein the fifth default value is less than the third default value and greater than the fourth default value, and the second pixel value is less than the first pixel value; and setting the pixel values of pixels having CT values in other ranges to zero.

13. The body region identification device of claim 9, wherein:

the preset machine learning model comprises at least one of a neural network model or a convolutional neural network model.

14. The body region identification device of claim 9, wherein the processor determines whether the numerical values of the medical image are abnormal by:
performing linear regression analysis on the bio-section images to obtain a linear regression equation, wherein Computed Tomography (CT) scan numbers are set as the independent variable, and the numerical values corresponding to the CT scan numbers are set as the dependent variable;
calculating a slope, a y-intercept, and a coefficient of determination of the linear regression equation;
determining whether the slope, the y-intercept, and the coefficient of determination in the linear regression equation are within respective predetermined ranges;
determining that the numerical values are abnormal if at least one of the slope, the y-intercept, and the coefficient of determination exceeds the respective predetermined range; and
determining that the numerical values are not abnormal if none of the predetermined ranges are exceeded.

15. The body region identification device of claim 14, wherein the processor adjusts the numerical values by:
establishing a two-dimensional coordinate system with the CT scan number as the independent variable and the numerical value of the body region as the dependent variable;
generating a first plotline in the two-dimensional coordinate system according to the CT scan numbers and the respective numerical values of the body regions;
equally dividing the first plotline to obtain an N number of segments;
performing linear regression analysis on each of the N number of segments to obtain an N number of linear regression equations, respectively, wherein each of the N number of linear regression equations comprises a slope, a y-intercept, and a coefficient of determination;
determining qualified linear regression equations of the N number of linear regression equations, wherein the qualified linear regression equations are the linear regression equations of the N number of linear regression equations in which the slope, the y-intercept, and the coefficient of determination are respectively within the predetermined ranges;
calculating an average of the slopes and y-intercepts of all of the qualified linear regression equations to obtain an average slope and an average y-intercept;
generating a second plotline according to the average slope and the average y-intercept, and adjusting the numerical values corresponding to the TC scan numbers according to the second plotline.

16. The body region identification device of claim 15, wherein the processor adjusts the numerical values by:
determining whether the numerical values are abnormal after the adjustment; and
outputting a notification to perform manual adjustment if the numerical values are abnormal.

* * * * *